United States Patent
Bolan et al.

(10) Patent No.: US 9,795,455 B2
(45) Date of Patent: Oct. 24, 2017

(54) TISSUE MARKER FOR MULTIMODALITY RADIOGRAPHIC IMAGING

(71) Applicant: Breast-Med, Inc., Golden Valley, MN (US)

(72) Inventors: Patrick Bolan, Minneapolis, MN (US); Mark C. Gross, Chaska, MN (US); Daniel A. Halpern, St. Louis Park, MN (US); Michael T. Nelson, Golden Valley, MN (US)

(73) Assignee: Breast-Med, Inc., Minnetonka, MN (US)

( * ) Notice: Subject to any disclaimer, the term of this patent is extended or adjusted under 35 U.S.C. 154(b) by 245 days.

(21) Appl. No.: 14/466,010

(22) Filed: Aug. 22, 2014

(65) Prior Publication Data

US 2016/0051337 A1 Feb. 25, 2016

(51) Int. Cl.
*A61B 5/05* (2006.01)
*A61B 90/00* (2016.01)
(Continued)

(52) U.S. Cl.
CPC .............. *A61B 90/39* (2016.02); *A61B 19/54* (2013.01); *A61B 2017/00004* (2013.01);
(Continued)

(58) Field of Classification Search
CPC . A61B 90/39; A61B 19/54; A61B 2090/3954; A61B 2090/3933;
(Continued)

(56) References Cited

U.S. PATENT DOCUMENTS

| | | | |
|---|---|---|---|
| 2,678,195 | A | 5/1954 | George et al. |
| 5,016,639 | A | 5/1991 | Allen |

(Continued)

FOREIGN PATENT DOCUMENTS

| | | |
|---|---|---|
| CA | 2579914 A1 | 11/2006 |
| EP | 1491147 A1 | 12/2004 |

(Continued)

OTHER PUBLICATIONS

"U.S. Appl. No. 14/022,539, Notice of Allowance mailed Oct. 24, 2014", 10 pgs.

(Continued)

*Primary Examiner* — Sanjay Cattungal
(74) *Attorney, Agent, or Firm* — Schwegman Lundberg & Woessner, P.A.

(57) ABSTRACT

A radiographic marker containing a sensing medium that initially includes a gas and liquid mixture for producing increased signal intensity in a first imaging modality. The radiographic marker can have a permeable portion allowing the exchange of the gases or liquids of the sensing medium to be changed or exchanged for at least a second fluid in the surrounding tissue to reduce the bubbles or air pockets created by the gas portion of the sensing medium. The change or exchange of gas for the second liquid in the radiographic marker produces a detectable signal intensity of the radiographic marker in a second imaging modality different from the first imaging modality.

34 Claims, 2 Drawing Sheets

(51) Int. Cl.
*A61B 19/00* (2006.01)
*A61B 17/00* (2006.01)

(52) U.S. Cl.
CPC ............... *A61B 2019/5433* (2013.01); *A61B 2019/5466* (2013.01); *A61B 2019/5495* (2013.01); *A61B 2090/3925* (2016.02); *A61B 2090/3933* (2016.02); *A61B 2090/3954* (2016.02); *A61B 2090/3966* (2016.02); *A61B 2090/3995* (2016.02)

(58) Field of Classification Search
CPC .... A61B 2090/3925; A61B 2090/3966; A61B 2019/5433; A61B 2017/00004; A61B 2019/5495; A61B 2019/5466; A61B 2090/3995
USPC .................................................. 600/407–431
See application file for complete search history.

(56) References Cited

U.S. PATENT DOCUMENTS

| | | | |
|---|---|---|---|
| 5,097,839 A | 3/1992 | Allen | |
| 5,119,817 A | 6/1992 | Allen | |
| 5,179,955 A | 1/1993 | Leveen et al. | |
| 5,211,164 A | 5/1993 | Allen | |
| 5,394,457 A | 2/1995 | Leibinger et al. | |
| 5,397,329 A | 3/1995 | Allen | |
| 5,405,402 A | 4/1995 | Dye et al. | |
| 5,469,847 A | 11/1995 | Zinreich et al. | |
| 5,609,850 A | 3/1997 | Deutsch et al. | |
| 5,702,128 A | 12/1997 | Maxim et al. | |
| 5,769,861 A | 6/1998 | Vilsmeier | |
| 5,782,764 A | 7/1998 | Werne | |
| 6,128,522 A | 10/2000 | Acker et al. | |
| 6,161,034 A | 12/2000 | Burbank et al. | |
| 6,181,960 B1 | 1/2001 | Jensen et al. | |
| 6,269,148 B1 | 7/2001 | Jessop et al. | |
| 6,270,464 B1 | 8/2001 | Fulton, III et al. | |
| 6,333,971 B2 | 12/2001 | McCrory et al. | |
| 6,347,241 B2 | 2/2002 | Burbank et al. | |
| 6,350,244 B1 | 2/2002 | Fisher | |
| 6,356,782 B1 | 3/2002 | Sirimanne et al. | |
| 6,371,904 B1 | 4/2002 | Sirimanne et al. | |
| 6,374,132 B1 | 4/2002 | Acker et al. | |
| 6,394,965 B1 | 5/2002 | Klein | |
| 6,405,072 B1 | 6/2002 | Cosman | |
| 6,419,680 B1 | 7/2002 | Cosman et al. | |
| 6,427,081 B1 | 7/2002 | Burbank et al. | |
| 6,487,438 B1 | 11/2002 | Widmark et al. | |
| 6,516,211 B1 | 2/2003 | Acker et al. | |
| 6,544,185 B2 | 4/2003 | Montegrande | |
| 6,546,279 B1 | 4/2003 | Bova et al. | |
| 6,549,802 B2 | 4/2003 | Thornton | |
| 6,567,689 B2 | 5/2003 | Burbank et al. | |
| 6,575,991 B1 | 6/2003 | Chesbrough et al. | |
| 6,605,047 B2 | 8/2003 | Zarins et al. | |
| 6,632,176 B2 | 10/2003 | McIntire et al. | |
| 6,635,064 B2 | 10/2003 | U et al. | |
| 6,656,192 B2 | 12/2003 | Espositio et al. | |
| 6,662,041 B2 | 12/2003 | Burbank et al. | |
| 6,699,205 B2 | 3/2004 | Fulton, III et al. | |
| 6,725,083 B1 | 4/2004 | Burbank et al. | |
| 6,730,042 B2 | 5/2004 | Fulton et al. | |
| 6,746,661 B2 | 6/2004 | Kaplan | |
| 6,761,679 B2 | 7/2004 | Sajo et al. | |
| 6,773,408 B1 | 8/2004 | Acker et al. | |
| 6,778,850 B1 | 8/2004 | Adler et al. | |
| 6,862,470 B2 | 3/2005 | Burbank et al. | |
| 6,927,406 B2 | 8/2005 | Zyromski | |
| 6,993,375 B2 | 1/2006 | Burbank et al. | |
| 6,996,433 B2 | 2/2006 | Burbank et al. | |
| 7,010,340 B2 | 3/2006 | Scarantino et al. | |
| 7,044,957 B2 | 5/2006 | Foerster et al. | |
| 7,047,063 B2 | 5/2006 | Burbank et al. | |
| 7,226,442 B2 | 6/2007 | Sheppard, Jr. et al. | |
| 7,668,582 B2 | 2/2010 | Sirimanne et al. | |
| 7,702,378 B2 * | 4/2010 | Bolan .................. | A61B 19/54 600/414 |
| 7,792,568 B2 | 9/2010 | Zhong et al. | |
| 8,280,486 B2 | 10/2012 | Miller et al. | |
| 8,544,162 B2 | 10/2013 | Bolan et al. | |
| 8,966,735 B2 | 3/2015 | Bolan et al. | |
| 9,241,773 B2 | 1/2016 | Bolan et al. | |
| 2002/0035324 A1 | 3/2002 | Sirimanne et al. | |
| 2002/0083591 A1 | 7/2002 | Geertsma et al. | |
| 2002/0083951 A1 | 7/2002 | Stegmaier et al. | |
| 2002/0107437 A1 | 8/2002 | Sirimanne et al. | |
| 2002/0161298 A1 | 10/2002 | Burbank et al. | |
| 2002/0188196 A1 | 12/2002 | Burbank et al. | |
| 2004/0030262 A1 | 2/2004 | Fisher et al. | |
| 2004/0176684 A1 | 9/2004 | Tabuchi et al. | |
| 2004/0186377 A1 | 9/2004 | Zhong et al. | |
| 2004/0193044 A1 | 9/2004 | Burbank et al. | |
| 2004/0236211 A1 | 11/2004 | Burbank et al. | |
| 2004/0236212 A1 | 11/2004 | Jones et al. | |
| 2004/0236213 A1 | 11/2004 | Jones et al. | |
| 2005/0004456 A1 | 1/2005 | Thomas et al. | |
| 2005/0020916 A1 | 1/2005 | MacFarlane et al. | |
| 2005/0033157 A1 | 2/2005 | Klein et al. | |
| 2005/0059884 A1 | 3/2005 | Kragg | |
| 2005/0059888 A1 | 3/2005 | Sirimanne et al. | |
| 2005/0065393 A1 | 3/2005 | Miller | |
| 2005/0080337 A1 | 4/2005 | Sirimanne et al. | |
| 2005/0080338 A1 | 4/2005 | Sirimanne et al. | |
| 2005/0080339 A1 | 4/2005 | Sirimanne et al. | |
| 2005/0085724 A1 | 4/2005 | Sirimanne et al. | |
| 2005/0143656 A1 | 6/2005 | Burbank et al. | |
| 2005/0154293 A1 | 7/2005 | Gisselberg et al. | |
| 2005/0205445 A1 | 9/2005 | Seiler et al. | |
| 2005/0234336 A1 | 10/2005 | Beckman et al. | |
| 2005/0255045 A1 | 11/2005 | Woltering | |
| 2006/0036165 A1 | 2/2006 | Burbank et al. | |
| 2006/0058645 A1 | 3/2006 | Komistek et al. | |
| 2006/0058648 A1 | 3/2006 | Meier et al. | |
| 2006/0079805 A1 | 4/2006 | Miller et al. | |
| 2006/0084865 A1 | 4/2006 | Burbank et al. | |
| 2006/0122503 A1 | 6/2006 | Burbank et al. | |
| 2006/0155190 A1 | 7/2006 | Burbank et al. | |
| 2006/0173296 A1 | 8/2006 | Miller et al. | |
| 2006/0293581 A1 | 12/2006 | Plewes et al. | |
| 2007/0087026 A1 | 4/2007 | Field | |
| 2007/0093726 A1 | 4/2007 | Leopold et al. | |
| 2007/0110665 A1 | 5/2007 | Bolan et al. | |
| 2007/0118034 A1 | 5/2007 | Mark | |
| 2007/0142725 A1 | 6/2007 | Hardin et al. | |
| 2008/0033286 A1 | 2/2008 | Whitmore et al. | |
| 2008/0234572 A1 | 9/2008 | Jones | |
| 2008/0269603 A1 | 10/2008 | Nicoson et al. | |
| 2009/0069670 A1 | 3/2009 | Mark | |
| 2009/0105584 A1 | 4/2009 | Jones | |
| 2010/0030072 A1 | 2/2010 | Casanova et al. | |
| 2010/0121225 A1 * | 5/2010 | Lewkowicz ........... | A61B 1/041 600/593 |
| 2010/0287887 A1 | 11/2010 | Bolan et al. | |
| 2011/0276070 A1 | 11/2011 | Viray et al. | |
| 2013/0046164 A1 | 2/2013 | Liu et al. | |
| 2013/0150707 A1 | 6/2013 | Cima et al. | |
| 2013/0324946 A1 | 12/2013 | Tobias et al. | |
| 2014/0187911 A1 | 7/2014 | Bolan et al. | |
| 2015/0173848 A1 | 6/2015 | Bolan et al. | |
| 2016/0100910 A1 | 4/2016 | Bolan et al. | |

FOREIGN PATENT DOCUMENTS

| | | |
|---|---|---|
| EP | 1579878 A1 | 9/2005 |
| EP | 1847845 A1 | 10/2007 |
| WO | WO-9717103 A1 | 5/1997 |
| WO | WO-0024332 A1 | 5/2000 |
| WO | WO-0038579 A2 | 7/2000 |
| WO | WO-0230482 A1 | 4/2002 |
| WO | WO-03022133 A2 | 3/2003 |
| WO | WO-03051452 A1 | 6/2003 |
| WO | WO-2004084738 A1 | 10/2004 |

(56) References Cited

FOREIGN PATENT DOCUMENTS

| WO | WO-2005046733 A1 | 5/2005 |
|---|---|---|
| WO | WO-2005063126 A2 | 7/2005 |
| WO | WO-2006044132 A1 | 4/2006 |
| WO | WO-2006119645 A1 | 11/2006 |
| WO | WO-2007060576 A2 | 5/2007 |
| WO | WO-2016028976 A1 | 2/2016 |
| WO | WO-2016028976 A8 | 2/2016 |

OTHER PUBLICATIONS

"U.S. Appl. No. 14/634,965, Non Final Office Action mailed May 20, 2015", 10 pgs.
"U.S. Appl. No. 14/634,965, Notice of Allowance mailed Sep. 15, 2015", 10 pgs.
"U.S. Appl. No. 14/634,965, Preliminary Amendment filed Mar. 3, 2015", 9 pgs.
"U.S. Appl. No. 14/634,965, Response filed Apr. 28, 2015 to Restriction Requirement filed Apr. 8, 2015", 9 pgs.
"U.S. Appl. No. 14/634,965, Response filed Aug. 18, 2015 to Non Final Office Action mailed May 20, 2015", 12 pgs.
"U.S. Appl. No. 14/634,965, Restriction Requirement mailed Apr. 8, 2015", 7 pgs.
"U.S. Appl. No. 14/966,400, Preliminary Amendment filed Dec. 15, 2015", 6 pgs.
"International Application Serial No. PCT/US2015/046038, International Search Report mailed Oct. 21, 2015", 4 pgs.
"International Application Serial No. PCT/US2015/046038, Written Opinion mailed Oct. 21, 2015", 7 pgs.
Bolan, Patrick, "A Novel Tissue Marker for Multimodal Breast Imaging (Abstract)", Abstract submitted Apr. 2005, published Radiological Society of North America (RSNA), Nov. 2005., [Online]. Retrieved from the Internet: <URL: http://abstract.rsna.org/index.cfm?fuseaction=submission.popupPrevie . . . >, (Nov. 2005), 2 pgs.
Bolan, Patrick, "Soft Tissue Markers or Clips (Presentation)", This work was supported under NIH grants, the MIND institute, and the Keck Foundation., (Nov. 16, 2005), 16 pgs.
"U.S. Appl. No. 11/281,801, Examiner Interview Summary mailed Sep. 2, 2009", 4 pgs.
"U.S. Appl. No. 11/281,801, Final Office Action mailed Mar. 13, 2009", 18 pgs.
"U.S. Appl. No. 11/281,801, Non-Final Office Action mailed Sep. 22, 2008", 12 pgs.
"U.S. Appl. No. 11/281,801, Notice of Allowance mailed Dec. 2, 2009", 10 pgs.
"U.S. Appl. No. 11/281,801, Response filed Dec. 18, 2008 to Non-Final Office Action mailed Sep. 22, 2008", 25 pgs.
"U.S. Appl. No. 11/281,801, Response filed Jun. 12, 2009 to Final Office Action mailed Mar. 13, 2009", 27 pgs.
"U.S. Appl. No. 11/281,801, Response filed Jul. 17, 2008 to Restriction Requirement mailed Apr. 17, 2008", 13 pgs.
"U.S. Appl. No. 11/281,801, Restriction Requirement mailed Apr. 17, 2008", 5 pgs.
"U.S. Appl. No. 11/281,801, Supplemental Response filed Aug. 24, 2009 to Final Office Action mailed Mar. 13, 2009", 29 pgs.
"U.S. Appl. No. 11/281,801, Supplemental Response filed Aug. 25, 2009 to Final Office Action mailed Mar. 13, 2009", 2 pgs.
"U.S. Appl. No. 11/281,801, Supplemental Response filed Aug. 28, 2009 to Final Office Action mailed Mar. 13, 2009", 16 pgs.
"U.S. Appl. No. 12/762,837, Non Final Office Action mailed Nov. 2, 2012", 15 pgs.
"U.S. Appl. No. 12/762,837, Notice of Allowance mailed May 30, 2013", 6 pgs.
"U.S. Appl. No. 12/762,837, Response filed Jan. 18, 2013 to Non Final Office Action mailed Nov. 2, 2012", 14 pgs.
"U.S. Appl. No. 14/022,539, Final Office Action mailed Jul. 24, 2014", 7 pgs.
"U.S. Appl. No. 14/022,539, Non Final Office Action mailed Apr. 11, 2014", 8 pgs.
"U.S. Appl. No. 14/022,539, Preliminary Amendment filed Mar. 10, 2014", 8 pgs.
"U.S. Appl. No. 14/022,539, Response filed Jul. 11, 2014 to Non Final Office Action mailed Apr. 11, 2014", 10 pgs.
Bolan, P. J., et al., "A Novel Soft Tissue Marker for Multimodal Breast Imagine with Positive MRI Contrast", Joint Annual Meeting ISMRM-ESMRMB, (May 2007), 1 pg.
Ellis, R. E., et al., "Use of Biocompatible Fiducial Marker in Evaluating the Accuracy of CT Image Registration", Investigative Radiology, (1996), 1-9.
Frank, Steven J., et al., "A Novel MRI Marker for Prostate Brachytherapy", Int. J. Radiation Oncology Biol. Phys., vol. 70, No. 1, (2008), 5-8.
Gierga, D. P., et al., "The Correlation between Internal and External Markers for Abdominal Tumors: Implications for Respiratory Gating", Int J Radiat Oncol Biol Phys.; 61 (f); 1551-8, (Apr. 1, 2005), 1 pg.
Igdem, S., et al., "Implantation of Fiducial Markers for Image Guidance in Prostate Radiotherapy: Patient-reported toxicity", The British Journal of Radiology, (2009), 1-5.
Maier-Hein, L, et al., "On Combining Internal and External Fiducials for Liver Motion Compensation", Comput Aided Surg.; 13(6): 369-76, (Nov. 2008), 1 pg.
"U.S. Appl. No. 14/966,400, Non Final Office Action dated May 2, 2017", 10 pgs.
"U.S. Appl. No. 14/966,400, Notice of Allowance dated Aug. 30, 2017", 5 pgs.
"U.S. Appl. No. 14/966,400, Response filed Aug. 2, 2017 to Non Final Office Action dated May 2, 2017", 9 pgs.

\* cited by examiner

TISSUE MARKER FOR MULTIMODALITY RADIOGRAPHIC IMAGING

TECHNICAL FIELD

This document pertains generally, but not by way of limitation, to tissue markers. More particularly, this document relates to implantable tissue markers for use in imaging applications.

BACKGROUND

Certain medical conditions, such as breast cancer, are increasingly being diagnosed with minimally invasive medical techniques. Such techniques typically involve the use of clinical imaging methods that allow visualization of interior portions of a patient's body without excessive incisions and biopsies, which can cause avoidable collateral damage to healthy tissue adjacent the affected tissue. Imaging techniques can include a variety of modalities, including, for example, X-rays, computed tomographic ("CT") X-ray imaging, fluoroscopy, portal film imaging devices, electronic portal imaging devices, ultrasound, electrical impedance tomography ("EIT"), magnetic resonance ("MR") imaging ("MRI"), magnetic source imaging ("MSI"), magnetic resonance spectroscopy ("MRS"), magnetic resonance angiography ("MRA"), magneto electro-encephalography ("MEG"), laser optical imaging, electric potential tomography ("EPT"), brain electrical activity mapping ("BEAM"), arterial contrast injection angiography, digital subtraction angiography, positron emission tomography ("PET") and single photon emission computed tomography ("SPECT").

Certain imaging modalities involve the use of radiographic markers. Radiographic markers are implantable devices that are implanted into the patient through either percutaneous injection or surgical placement procedure. Typically, radiographic markers include one or more solid objects, such as a metallic wire or ceramic beads, that are implanted individually or as a plurality of objects suspended in a gelatinous matrix, collagen, or polylactic acid. The solid objects can temporarily increase visibility of the marker to certain imaging modalities such as ultrasound imaging. The markers can be readily detected by imaging modalities and are typically shaped into an artificial shape such that the marker can be distinguished from naturally occurring anatomical structures in the patient's body. For example, the markers can have artificial shapes such as coils, stars, rectangles, spheres or other artificial shapes that do not naturally occur in anatomical structures. The markers provide a reference point or landmark for physicians to localize a biopsy or surgical site in subsequent imaging studies or to facilitate image registration during image-guided therapeutic procedures.

Certain conventional markers appear as signal voids or dark artifacts when imaged with magnetic resonance imaging. However, the dark appearance of conventional markers can be difficult to distinguish and identify when imaging certain tissue or when searching for certain medical conditions. For example, heterogeneous breast tissue ordinarily produces numerous dark artifacts when imaged with MR imaging. The numerous dark artifacts normally occurring in the heterogeneous breast tissue can make the identifying dark artifacts of the markers difficult. Certain markers produce large susceptibility artifacts under MR imaging, which can distort images when MRI and spectroscopic modalities are employed. Certain markers can incorporate an external composition or coating that produces a positive or bright signal when imaged. However, the external composition is typically bio-absorbable and begins to dissipate soon after implantation gradually reducing the effectiveness of the marker.

OVERVIEW

The present inventors have recognized, among other things, that a problem to be solved can include that conventional radiographic markers for providing reference points for follow-up procedures can be difficult to visualize over time or can be less effective as radiographic markers depending on the imaging modality. In particular, radiographic markers are often initially positioned using a first imaging modality while follow up procedures are often performed with a different second imaging modality. In an example, the present subject matter can provide a solution to this problem, such as by a radiographic marker includes a sensing medium within the radiographic marker having a gas and liquid mixture that produces a detectable signal intensity in a first imaging modality at a first time. Over a predetermined time period, the ratio of gas to liquid of the sensing medium is modified to produce a detectable signal intensity in a second imaging modality different from the first imaging modality. This arrangement allows the radiographic marker to be efficiently positioned using a first imaging modality, while the radiographic marker that can be effectively located or referenced in follow up procedures employing different imaging modalities.

In an example, the sensing medium in the radiographic marker can comprise a gas portion and a first liquid such that the sensing medium produces a detectable signal intensity under ultrasound imaging for initial position of the radiographic marker. In this configuration, the radiographic marker comprises a semipermeable chamber wall permitting transfer of gas and at least a second liquid across the chamber wall to modify the ratio of gas to liquid of the sensing medium such that the sensing medium is primarily a liquid following a predetermined time period such that the sensing medium produces detectable signal intensity under MRI for follow up procedures. The first and second liquids can comprise the same or different liquids. In other examples, the liquids can be condensed from gases or vapor entering the internal chamber.

A radiographic marker, according to an example of the present subject matter, includes a container wall enclosing an internal chamber and including a permeable portion and a sensing medium received within the internal chamber, the sensing medium including a first liquid and a gas portion. The permeable portion permits transfer of the gas portion and a second liquid across the chamber wall to change a ratio of fluid to liquid of the sensing medium within the internal chamber.

A method of making a radiographic marker, according to an example of the present subject matter, includes providing a chamber wall defining an internal chamber, the chamber wall including a permeable portion. The method also includes at least partially filling the internal chamber with a sensing medium having a first liquid, wherein a gas portion permeates through the permeable portion over a predetermined time period such that the sensing medium comprises a gas and liquid mixture. The method can also include sealing the chamber wall to enclose the internal chamber.

This overview is intended to provide an overview of subject matter of the present patent application. It is not intended to provide an exclusive or exhaustive explanation of the present subject matter. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1:
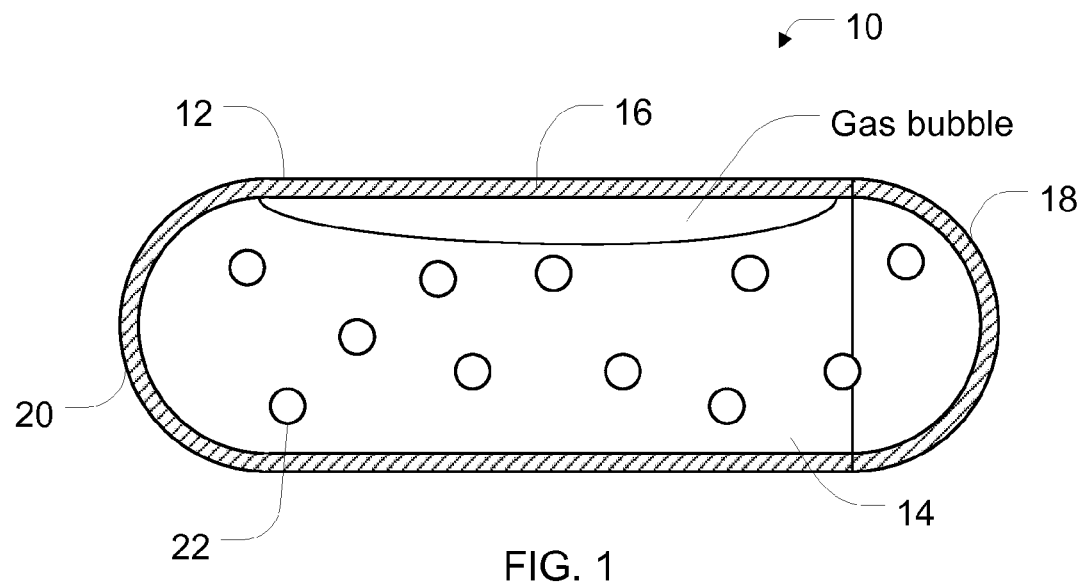
FIG. 1 is a side cross-sectional view of a radiographic marker.

As depicted in FIGS. 1-4, a radiographic marker 10, according to an example, can include a container wall 12 shaped into a tubular shape so as to define an internal chamber 14 for a sensing medium comprising at least a first liquid producing a detectable signal intensity in at least one imaging modality. In an example, the radiographic marker 10 can be sized and shaped for insertion via a biopsy cannula. In certain examples, the radiographic marker 10 can have a major dimension of about 3 mm to 4 mm and a minor dimension of about 1 mm to 2 mm. The container wall 12 can include a permeable portion 16 permitting the exchange of certain gases or liquids and a second liquid through the container wall 12. For the purposes of this disclosure, the first liquid refers to liquid initially present in the radiographic marker 10 at implantation and the second liquid refers to liquid permeating into the device through the permeable portion 16 after implantation. In various examples of the present subject matter, the first and second liquid can comprise the same chemical composition, different chemical composition, the same concentration of various components, different concentration of various components and the like. The internal chamber 14 can be enclosed within the container wall 12 and configured to receive the sensing medium for providing detectable signal intensity when viewed with certain imaging modalities including, but not limited to x-rays, CT x-ray imaging, fluoroscopy, portal film imaging, electronic portal imaging, ultrasound, EIT, MRI, MSI, MRS, MRA, MEG, laser optical imaging, EPT, BEAM, arterial contrast injection angiography, digital subtraction angiography, PET and SPECT. In an example, the container wall 12 can comprise a material for producing detectable signal intensity when viewed in at least one imaging modality.

In an example, the chamber wall 12 can define a first end portion 18 and a second end portion 20, the first end portion 18 being initially opened such that sensing media can be fed into the interior of the container wall 12 before the first end portion 18 is sealed for form the interior chamber 14. In certain examples, the first end is sealed with a permanent biocompatible adhesive including, but not limited to cyanoacrylate, or physical welding techniques.

In an example, the sensing medium includes a first liquid detectable by at least one imaging modality. In at least some examples, the gas portion is initially sealed within inner chamber 14 with the first liquid to form a gas and liquid mixture. In other examples, the gas portion permeates through the container wall 12 after implantation of the radiographic marker 10 to form a gas and liquid mixture. In an example, the gas portion forms a bubble or plurality of bubbles within the internal chamber 14. The bubble or bubbles formed within the internal chamber 14 improves the detectability of the signal intensity of the radiographic marker 10 with certain imaging modalities, such as ultrasound imaging. In an example, the gas portion can initially comprise the total volume of the internal chamber 14. In other examples, the internal chamber 14 can initially filed with liquid such that the internal chamber 14 is entirely liquid or comprises a gas liquid mixture. In an example, the gas portion can comprise 0-100% of the total volume of the internal chamber 14.

In an example, the gas portion can comprise oxygen, nitrogen, hydrogen, carbon dioxide, inert gases and various combinations thereof. In an example, the first liquid can comprise water, fluorocarbons, alcohols, acetones, DMSO or other solvents. In other examples, the first liquid can comprise a gel material; a paste; a colloid; or other solid or semi-solid material that produces a detectable signal intensity when evaluated with at least one imaging modality. The materials of the sensing medium can be selected to customize the appearance of the radiographic marker in different imaging modalities and under different conditions, e.g., with or without contrast, and in various tissue types.

In an example, the first liquid of the sensing medium can comprise an immiscible liquid colloid of at least two immiscible liquids. In this configuration, the interface between the at least two immiscible liquids produces a detectable signal when viewed with at least one imaging modality.

In an example, the permeable portion 16 of the container wall 12 can permit the exchange of gases and/or liquids within the internal chamber 14 with a second liquid in the surrounding tissue. In an example, the second liquid can comprise water or other aqueous solutions. The transfer of the second liquid into the internal chamber can produce a change in the size of the gas bubble or bubbles through one or more physical processes, including mass transfer of the gas out of the internal chamber, as well as changes in pressure, gas solubility within the chamber. This exchange process can reduce the size of the bubble or bubbles created by the gas portion and increase liquid composition of the sensing medium, thereby increasing the signal intensity of the radiographic marker 10 with certain imaging modalities, such as MRI, over a predetermined period of time. In certain examples, the predetermined period of time can correspond to the time between the implantation of the radiographic marker and a first follow up procedure. In this configuration, the radiographic marker can be positioned within the tissue with the benefit of a first imaging modality, such as ultrasound imaging, and located within the tissue at a follow up procedure with a second imaging modality, such as MRI. This arrangement allows use of a first imaging modality or modalities for positioning the radiographic marker 10 and a second imaging modality or different imaging modalities for relocating the radiographic marker 10 when performing subsequent evaluations or procedures. The permeability of the container wall 12 can control the rate of exchange of gases for second liquid through the container wall 12. In certain examples, the container wall 12 can include, but is not limited to poly-ethyl ethyl ketone ("PEEK"), silicone, polyurethane, PTFE, other polymers, glasses, ceramics, metals, composites and other advanced materials.

In an example, the container wall 12 can comprise a biocompatible material that can be implanted within living tissue without impacting the normal function of the tissue. In an example, the container wall 12 can define an interior surface and an exterior surface. A biocompatible coating can be applied to the exterior surface to improve biocompatibility, promote specific biological interactions such as fibrogenesis, or increase lubricity to improve the ability to place the radiographic marker 10. A coating can also be applied to either the interior or exterior surfaces to regulate permeation across the permeable portion 16 of the container wall 12. In an example, the coating can comprise silicone, polyurethane, parylene, and other hydrophilic or hydrophobic materials.

In an example, the container wall 12 can comprise a bio-absorbable coating on the exterior surface of the container wall 12 for temporarily providing detectable signal intensity in at least one imaging modality. In an example, the bio-absorbable coating comprises polylactic acid ("PLA"), collagen, beta-glucan or other bio-absorbable materials.

Figure 2:
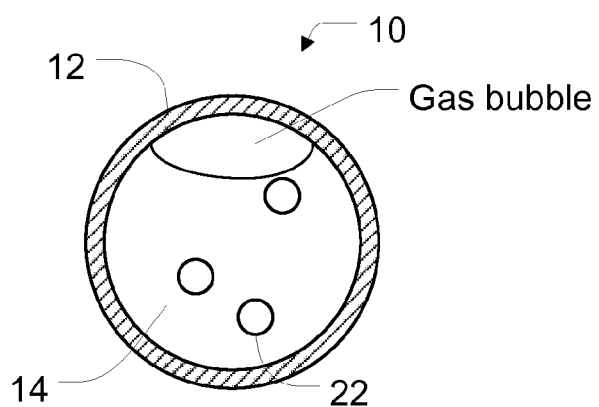
FIG. 2 is an axial cross-sectional view of the radiographic marker of FIG. 1.
Figure 3:
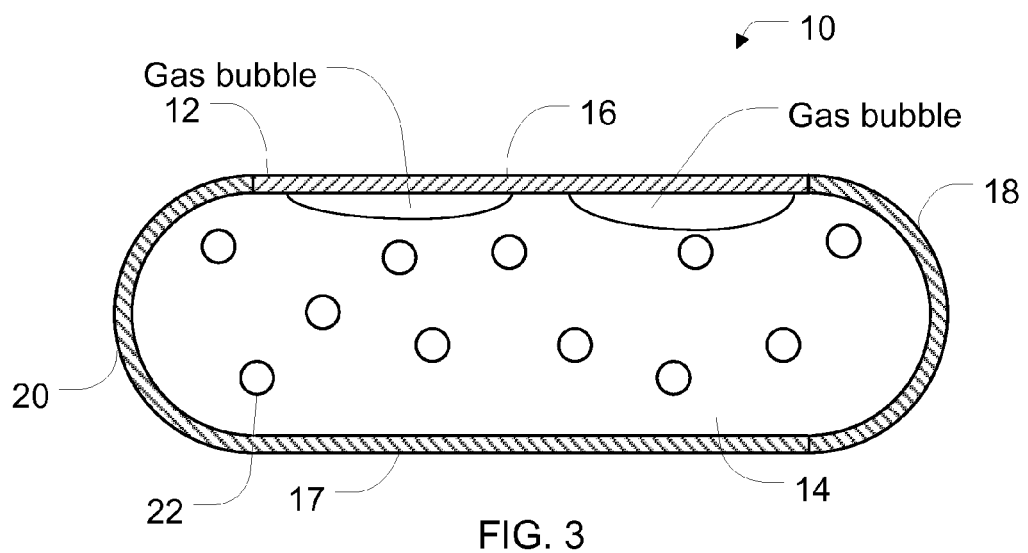
FIG. 3 is a side cross-sectional view of a radiographic marker.
Figure 4:
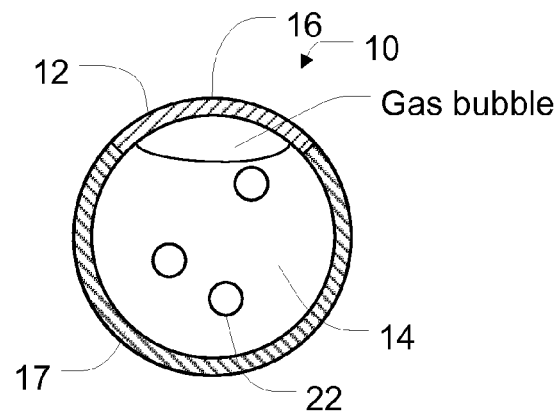
FIG. 4 is an axial cross-sectional view of the radiographic marker of FIG. 3.

In an example, the container wall 12 can comprise a gas or liquid permeable portion 16 and an impermeable portion 17 as depicted in FIGS. 3-4. In certain examples, the impermeable portion 17 can comprise glass, ceramics, impermeable polymers, silicones, metals and composites. In another example, the container wall 12 can comprise a plurality of permeable portions 16 separated by at least one impermeable portion 17. In yet another example, the container wall 12 can entirely comprise a permeable material as depicted in FIGS. 1-2.

In an example, the sensing medium can include an osmotic agent to increase the osmolarity within the internal chamber 14 to facilitate the change or exchange of liquids and/or other materials within the internal chamber 14 and second liquid in the surrounding tissue. In certain examples, the osmotic agent can include a salt, including, but not limited to sodium chloride, hyaluronic acid or other hydrophilic or hydrophobic osmotic agents, or desiccants and/or humectants for facilitating and or controlling the transfer of fluids across the chamber wall 12. The osmotic agent increases the osmolarity of the first liquid within the internal chamber 14 creating an osmotic pressure gradient that draws second liquid across the chamber wall 12 into the inner chamber 14 thereby pushing the gases through the chamber wall 12 and out of the inner chamber 14 or dissolving or compressing and thus reducing the gas volume in the chamber. The relative concentration of salt or solutes within the first liquid can be varied to change the rate of change or exchange of the liquid or gas portions for the surrounding second liquid. The type and concentration of salt or solutes in the first liquid can be varied to change the rate of change or exchange. In an example, the osmotic agent corresponds to a naturally occurring osmotic agent, such as sodium chloride, that is ordinarily dissolved within the second liquid. In this configuration, at least the initial concentration of the osmotic agent within the first fluid is greater than the normal concentration in the second fluid to facilitate permeation of the second fluid into the inner chamber 14.

In an example, the permeability of the permeable portion 16 of the container wall 12 can be configured to control the rate of change or exchange of the gas portion for surrounding second liquid. In certain examples, the container wall 12 can include different materials or different combinations of material to change the effective permeability of the permeable portion 16 of the container wall 12 to change the rate of exchange.

In an example, the sensing medium can include at least one contrast agent including, but not limited to lanthanide elements, such as Europium or Dysprosium; iron oxides; lipids; perfluorocarbons; Gadolinium chelates; compounds containing other lanthanide elements, such as Europium or Dysprosium; iodinated CT contrast agents; other contrast agents that modulate signal intensity, chemical shift or MR relaxation rate and combinations thereof. In an example, the at least one contrast agent can comprise a MR contrast agent such as a Gadolinium-based MR contrast agent including, but not limited to MAGNEVIST MR contrast agent, commercially available from BERLEX of Montville, N.J.; OMNISCAN MR contrast agent commercially available from GE HEALTHCARE of Chalfont St. Giles, United Kingdom; and PROHANCE MR and OPTIMARK MR contrast agents commercially available from TYCO HEALTHCARE/MALLINCKRODT INC of St. Louis, Mo. In an example, the at least one contrast agent can comprise a CT contrast agent including, but not limited to OMNIPAQUE CT contrast agent commercially available from GE HEALTHCARE of Chalfont ST. Giles, United Kingdom; and HEXABRIX, TELEBRIX and CONRAY CT contrast agents commercially available from TYCO HEALTHCARE/MALLINCKRODT INC of St. Louis, Mo., or the generic chemicals used with each of these brands of contrast agent.

In an example, the permeable portion 16 of the container wall 12 is semi-permeable such that small molecules such as water or gases can permeate through the container wall 12 while large molecules, such as the contrast agent, are retained within the inner chamber 14. In an example, the volume of contrast agent in the internal chamber 14 can be maximized to promote visibility of the radiographic marker 10. The magnetic susceptibility of the at least one contrast agent and the magnetic susceptibility of the chamber wall 12 can be matched to further promote the visibility of the radiographic marker 10.

In an example, the chamber wall 12 can promote visibility with certain imaging modalities. In certain examples, the chamber wall 12 can include a radiopaque polymer that providers contrast in X-ray imaging modalities. In another example, a difference in acoustic impedance between the chamber wall 12 and the sensing material in the internal chamber 14 allows the radiographic marker 10 to reflect ultrasound waves, thereby promoting visibility in an ultrasound imaging modality. In yet another example, the magnetic susceptibility of the chamber wall 12 is matched to that of the sensing material in the internal chamber 14 and that of the surrounding tissue improving visibility in MRI modalities by improving magnetic field homogeneity and reducing $T_2^*$ artifacts.

In an example, the at least one contrast agent can be sensitive to changes in the physical properties of the surrounding tissue. The at least one contrast agent can undergo a chemical change when the physical parameters of the surrounding tissue change or a particular condition develops. The physical conditions that can be monitored for include, but are not limited to pH, temperature, oxygenation, particular targeted molecules and other physical ailments or conditions.

In an example, the sensing medium can include at least one therapeutic agent. The therapeutic agent can elute through the permeable portion 16 of the container wall 12 into the surrounding tissue at a predetermined rate. In certain examples, the contrast agent can be sensitive to at least one analyte in the surrounding tissue, including, but not limited to oxygen or hydrogen ions; estrogen or other proteins, drugs or hormones, nitric oxides and other small molecules permeable through the permeable membrane. In this configuration, the permeable membrane is configured to exchange the analyte.

In an example, the radiographic marker 10 can also include at least one object 22 positioned within the interior chamber 14. Each object 22 can include an artificial shape without a naturally occurring analog within the tissue to be marked with the radiographic marker 10. The objects 22 speed the identification of the radiographic markers 10 and avoid confusing the radiographic markers 10 with naturally occurring structures within the tissue.

In an example, at least one object 22 is capable of generating a detectable electromagnetic signal. In certain examples, the object 22 comprises an active transmitter or sensing device configured to independently transmit a detectable signal. In other examples, the object 22 comprises a passive transmitter or sensing device configured to transmit a detectable signal upon exposure to electromagnetic radiation including, but not limited to IR and ultraviolet radiation.

A method of making at least one radiographic marker 10 for implantation within a patient's body can comprise providing a chamber wall 12 defining an interior chamber 14, filling the interior chamber 14 with a sensing medium and sealing the interior chamber 14.

At the providing step, a chamber wall 12 defining an interior chamber 14 is provided. The chamber wall 12 can include an open first end 18 and a closed second end 20. In an example, a permeable portion 16 is formed in the chamber wall 12. In another example, an impermeable portion 17 is fused to at least one permeable portion 16 to form a chamber wall 12 having impermeable and permeable portions 16. In an example, at least one of the exterior or interior surface of the chamber wall 12 with a biocompatible coating. In an example, the chamber wall 12 is moldable from a biocompatible material.

At the filling step, a sensing medium is deposited within the interior chamber 14 through the open first end 18. In an example, the sensing medium initially includes a first fluid and a gas portion. In another example, the sensing medium can initially include a first fluid, whereas the gas portion permeates into the interior chamber 14 to form the gas portion within the interior chamber 14. In an example, the gas portion and the first fluid are phase separated such that the gas portion defines a single bubble or large bubbles in the first fluid. In another example, the gas portion and first fluid are mixed as a colloid. In an example, at least one object 22 having an artificial shape is deposited in the interior chamber 14.

At the sealing step, the first end 18 of the chamber wall 12 is sealed to enclose the interior chamber 14. In an example, the first end 18 of the chamber wall 12 is sealed with a biocompatible colloid. The interior chamber 14 is enclosed such that the sensing medium retains a gas portion to create a bubble or plurality of bubbles within the interior chamber 14.

At least one radiographic marker 10 can be implanted within a patient's body to provide reference points for imaging a target location within the patient's body. In operation, at least one radiographic marker 10 is implanted near the target location via a biopsy cannula, injection needle or other surgical implement. The radiographic markers 10 can be implanted using a plurality of conventional surgical techniques, including, but not limited to non-invasive medical procedures, biopsy procedures or injection.

In an example, each radiographic marker 10 includes a sensing medium within the internal chamber 14, the sensing medium initially including a gas portion. The gas portion providing detectable signal intensity when the radiographic marker 10 imaged under ultrasound imaging. In this configuration, ultrasound imaging is used to guide the implantation of the radiographic marker 10 at a desired reference point in the patient's body.

Over a predetermined period, liquid from the surrounding tissue permeates through the chamber wall 12 forcing from the container, dissolving or compressing the gas in the interior chamber 14. In an example, the sensing medium includes at least one osmotic agent for increasing the osmolarity within the interior chamber 14 to draw second liquid across the permeable chamber wall 12 into the interior chamber 14.

After a predetermined time period, an image of the target location is generated in an MRI modality. The modified sensing medium comprising a reduced gas portion and increased first liquid provides detectable signal intensity when the radiographic marker 10 is viewed with MRI modality. In certain examples, other imaging modalities can be used including, but not limited to CT, X-ray imaging, fluoroscopy, EIT, MR, MSI, MRS, MRA, MEG, laser optical imaging, EPT, BEAM, arterial contrast injection angiography, digital subtraction angiography, PET and SPECT.

In an example, multiple imaging modalities can be employed to provide positional information for the target location. In certain examples, the images of the target location and the radiographic markers 10 can be registered to align the coordinate systems of the images. In this configuration, any point in the imaged target location can be made to correspond to an identical address in each image. The registration process involves the use of rigid body transformation techniques, which requires information of at least three reference points in each image to produce three-dimensional images. The radiographic markers 10 can act as fiducial markers to mark these points in the images such that the fiducial markers can be used to correlate the spaces in each image, both with respect to physical space and with respect to the other images. In an example, the fiducial markers can also provide a constant frame of reference that is visible in each imaging modality to facilitate registration. The modification of the sensing medium through the exchange of the gas portion for second liquid improves signal intensity of the radiographic marker 10 to improve the accuracy of the collected image.

As demonstrated by the foregoing discussion, various examples of the present subject matter can provide certain advantages, particularly in the context of imaging heterogeneous breast tissue. For example, the mixture of gas and liquid in the sensing medium as initially implanted allows certain imaging modalities, such as ultrasound imaging, to be used to accurately position each radiographic marker 10 at the proper reference point. Similarly, the transition of the sensing medium to decrease the gas in the sensing medium produces an increase in signal intensity in an MR imaging modality to provide improved visualization characteristics without producing excessive artifacts and interfering with MR imaging techniques including, but not limited to MR spectroscopy, diffusion imaging, susceptibility weighted imaging, dynamic contrast imaging, spectroscopy imaging and perfusion imaging.

Similarly, in certain examples, the container wall 12 is semi-permeable to retain the contrast agent within the interior chamber 14 of the radiographic marker 10, thereby preventing absorption of the contrast agent into the patient's body. Similarly, the increased signal produced by the exchange of gases for second liquid in the radiographic marker improves the likelihood that the radiographic marker 10 can be more easily located in follow-up procedures.

VARIOUS NOTES & EXAMPLES

In an example, the radiographic marker 10 can include a container wall 12 comprising poly-ether ether ketone ("PEEK") to provide a semi-permeable membrane. The container wall 12 can define an enclosed interior space containing a sensing medium that can initially comprise a gas portion and a first liquid. The first liquid of the sensing medium can comprise water having a concentration of sodium chloride between about 0% to about 30% by volume.

Each of these non-limiting examples can stand on its own, or can be combined in any permutation or combination with any one or more of the other examples.

The above detailed description includes references to the accompanying drawings, which form a part of the detailed description. The drawings show, by way of illustration, specific embodiments in which the present subject matter can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the present subject matter should be determined with reference to the appended claims, along with the full scope of equivalents to which such claims are entitled.

What is claimed is:

1. A radiographic marker, comprising:
    a container wall enclosing an internal chamber and including a permeable portion; and
    a sensing medium received within the internal chamber, the sensing medium initially including at least one of a first liquid, a gas portion and a solid portion, the sensing medium configured to be detectable using a first imaging modality;
    wherein the permeable portion is semi-permeable to permit, when injected or surgically implanted into a patient's body, transfer of enough of a second liquid through the permeable portion of the chamber wall into the inner chamber while confining the sensing medium within the inner chamber to change a ratio of gas to liquid of the sensing medium within the internal chamber to produce a detectable change in signal intensity using a second imaging modality that is of a different type than the first imaging modality.

2. The radiographic marker of claim 1, wherein the gas portion of the sensing medium creates at least one bubble within the internal chamber to produce a detectable signal intensity in a first imaging modality.

3. The radiographic marker of claim 2, wherein the first imaging modality comprises ultrasound imaging.

4. The radiographic marker of claim 1, wherein transfer of the second liquid across the chamber wall produces a detectable signal intensity in a second imaging modality.

5. The radiographic marker of claim 4, wherein the second imaging modality comprises magnetic resonance imaging.

6. The radiographic marker of claim 1, wherein the sensing medium further includes an osmotic agent to create an osmotic gradient drawing the second fluid into the internal chamber through the permeable portion of the chamber walls.

7. The radiographic marker of claim 1, the sensing medium includes at least one contrast agent.

8. The radiographic marker of claim 7, wherein the permeable portion of the container wall retains the contrast agent within the internal chamber as the second fluid and the gas portion are exchanged through the container wall.

9. The radiographic marker of claim 1, wherein the gas portion is dispersed within the first liquid.

10. The radiographic marker of claim 1, wherein the sensing medium includes at least one of a solid and a gel.

11. The radiographic marker of claim 1, further comprising at least one object positioned within the internal chamber;
    wherein the object comprises an artificial shape identifiable under an imaging modality.

12. The radiographic marker of claim 11, wherein the at least one object positioned is configured to transmit an electromagnetic signal.

13. The radiographic marker of claim 1, wherein the permeable portion is a semi-permeable material.

14. The radiographic marker of claim 1, wherein the container wall comprises an impermeable portion.

15. The radiographic marker of claim 1, wherein the impermeable material is selected from at least one of glass, ceramics, polymers, metals and composites.

16. The radiographic marker of claim 1, wherein the container wall includes a seal enclosing the internal chamber.

17. The radiographic marker of claim 1, wherein the radiographic marker includes at least one therapeutic agent received within the internal chamber;
wherein the therapeutic agent elutes through the permeable portion of the container wall.

18. The radiographic marker of claim 1, wherein the radiographic marker is sized and shaped to fit within a lumen of a cannula configured to deliver the radiographic marker to a fully implanted location within the subject.

19. The radiographic marker of claim 1, wherein the contrast agent is sensitive of at least one analyte in tissue surrounding the radiographic marker;
wherein the analyte permeates through the permeable portion of the chamber wall.

20. The radiographic marker of claim 19, wherein the analyte is selected from a group consisting of hydrogen ions, oxygen molecules, nitric oxide, small organic molecules, proteins, hormones or therapeutic agents and combinations thereof.

21. The radiographic marker of claim 1, wherein the contrast agent is sensitive to at least one physical condition of the tissue surrounding the radiographic marker.

22. The radiographic marker of claim 21, wherein the physical condition is selected from a group consisting of pH, temperature, oxygenation, tissue perfusion and combinations thereof.

23. The radiographic marker of claim 1, wherein the first liquid and the second liquid are immiscible.

24. The radiographic marker of claim 1, wherein the permeable portion permits transfer of liquids and gases across the chamber wall.

25. The radiographic marker of claim 1, wherein the permeable portion includes a permeability that is configured to controllably limit transfer of the second liquid across the permeable portion of the chamber wall to inhibit or prevent a sensing artifact using the second imaging modality.

26. The radiographic marker of claim 1, wherein the permeable portion is configured to confine the sensing medium within the internal chamber.

27. The radiographic marker of claim 26, wherein the permeable portion is configured to retain an osmotic agent within the internal chamber.

28. A method of making a radiographic marker, comprising:
providing a chamber wall defining an internal chamber, the chamber wall including a permeable portion;
at least partially filling the internal chamber with a sensing medium initially including at least one of a first liquid, gas portion and a solid portion, the sensing medium configured to be detectable using a first imaging modality; and
sealing the chamber wall to enclose the internal chamber;
wherein the permeable portion is semi-permeable to permit, when injected or surgically implanted into a patient's body, transfer of enough of a second liquid through the permeable portion of the chamber wall into the inner chamber while confining the sensing medium within the inner chamber to change a ratio of gas to liquid of the sensing medium within the internal chamber to produce a detectable change in signal intensity using a second imaging modality that is of a different type than the first imaging modality.

29. The method of claim 28, wherein the gas portion of the sensing medium creates at least one bubble within the internal chamber to produce a detectable signal intensity in a first imaging modality.

30. The method of claim 29, wherein the first imaging modality comprises ultrasound imaging.

31. The method of claim 28, wherein the gas portion permeates through the permeable portion to change the gas to liquid ratio of the sensing medium to produce in detectable signal intensity in a second imaging modality.

32. The method of claim 31, wherein the second imaging modality comprises magnetic resonance imaging.

33. The method of claim 28, comprising applying a coating to at least one of an internal surface of the biocompatible container and an external surface of the biocompatible container.

34. The method of claim 28, comprising at least partially filling the internal chamber with the sensing medium within a chamber at a pressure other than ambient pressure.

* * * * *